United States Patent [19]

Komatsu et al.

[11] Patent Number: 4,536,337

[45] Date of Patent: Aug. 20, 1985

[54] PROCESS FOR THE PREPARATION OF QUINONES

[75] Inventors: Tatsuyoshi Komatsu, Kamakura; Shigeaki Numata, Yokohama; Toshihiko Sumino, Kawasaki; Katsumi Matsuzaki, Yokohama; Masao Narita, Yokohama; Katsuhiko Hioki, Yokohama, all of Japan

[73] Assignee: Kawasaki Kasei Chemicals Ltd., Tokyo, Japan

[21] Appl. No.: 596,695

[22] Filed: Apr. 4, 1984

[30] Foreign Application Priority Data

Apr. 11, 1983 [JP] Japan .................................. 58-64315
Jan. 28, 1984 [JP] Japan .................................. 59-14086

[51] Int. Cl.³ .................... C07C 50/02; C07C 50/10; C07C 50/16; C07C 50/22
[52] U.S. Cl. ............................. 260/396 R; 260/365; 260/369; 260/385; 260/687 R
[58] Field of Search .................. 260/396 R, 365, 369, 260/385, 687

[56] References Cited

U.S. PATENT DOCUMENTS

| | | | |
|---|---|---|---|
| 729,502 | 5/1903 | Moest | 260/396 R |
| 757,136 | 4/1904 | Moest | 260/385 |
| 3,873,580 | 3/1975 | Rennie | 260/385 |

FOREIGN PATENT DOCUMENTS

| | | | |
|---|---|---|---|
| 1132996 | 10/1980 | Canada | 260/396 R |
| 75828 | 4/1983 | European Pat. Off. | 260/396 R |
| 19178 | of 1903 | United Kingdom | 260/385 |
| 1192037 | 5/1970 | United Kingdom | 260/385 |
| 1203434 | 8/1970 | United Kingdom | 260/396 R |
| 1360904 | 7/1974 | United Kingdom | 260/385 |

Primary Examiner—Glennon H. Hollrah
Assistant Examiner—Raymond Covington
Attorney, Agent, or Firm—Oblon, Fisher, Spivak, McClelland & Maier

[57] ABSTRACT

A process for preparing a quinone, which comprises reacting a polynuclear aromatic hydrocarbon and a ceric salt in an aqueous acid solution in the presence of an organic solvent selected from the group consisting of chlorobenzene and an alkylbenzene represented by the general formula:

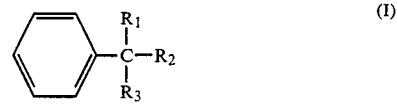

where each of $R_1$, $R_2$ and $R_3$ is an alkyl group and the total carbon number of the alkyl groups is from 3 to 6.

9 Claims, No Drawings

PROCESS FOR THE PREPARATION OF QUINONES

The present invention relates to a process for industrially advantageously preparing a quinone such as 1,4-naphthoquinone by reacting a polynuclear aromatic hydrocarbon such as naphthalene and a ceric salt in an aqueous acid solution in the presence of a certain water-immiscible inert organic solvent.

It is known that a polynuclear hydrocarbon such as naphthalene is oxidized by means of an aqueous acid solution of a ceric salt to form a quinone such as 1,4-naphthoquinone and the cerous salt thereby obtained is subjected to electrolytic oxidation to regenerate a ceric salt for reuse. Typical known processes are as follows:

(1) Japanese Examined Patent Publication No. 34978/1974 discloses a process in which a polynuclear aromatic hydrocarbon such as naphthalene is dissolved in an inert organic solvent immiscible with water and reacted with an aqueous acid solution of a ceric salt under stirring. As the water-immiscible inert (non-oxidative) organic solvent suitable for this process, this reference discloses only a saturated aliphatic hydrocarbon such as n-hexane; an ether such as diethyl ether; benzene; a chlorinated aliphatic hydrocarbon such as ethylene dichloride or methylene dichloride; and carbon tetrachloride. In particular, in the Examples given in this reference, only hexane, methylene chloride (i.e. methylene dichloride), ethylene dichloride and carbon tetrachloride are used among the above-mentioned inert organic solvents.

However, these solvents have drawbacks one way or another which may lead to serious practical problems. For example, the saturated aliphatic hydrocarbon has a difficulty that the desired product, i.e. a quinone such as 1,4-naphthoquinone, is hardly soluble therein; benzene is not only highly toxic but also reactive with the aqueous acid solution of a ceric salt; and the chlorinated aliphatic hydrocarbon has strong toxicity to human bodies and it is likely to decompose or undergo a property change when contacted with water or exposed to light and thereby generate hydrogen chloride which corrodes the apparatus. Further, each of the chlorinated aliphatic hydrocarbon and carbon tetrachloride has a relatively great specific gravity, and when the reaction is conducted in the presence of such a solvent in an aqueous acid solution having a high concentration of a ceric salt, the solvent layer in which the quinone as the desired reaction product is dissolved, will descend and mingle with the precipitates of the cerous salt formed by the reaction and will be hardly separable.

(2) Japanese Unexamined Patent Publication No. 61321/1981 discloses a process which is an improvement over the process discussed in the above (1) and in which powdery naphthalene is suspended in an aqueous acidic solution of a ceric salt by means of a dispersing agent and thus reacts with the ceric salt. However, this process has drawbacks that the reaction is slow and requires several hours for its completion, and that the formed quinone such as 1,4-naphthoquinone is gradually oxidized to form by-products, whereby the yield of the quinone will be lowered and it will be necessary to separate and remove the by-products.

The present inventors have conducted extensive researches to overcome the conventional drawbacks and to provide an industrially advantageous process for the preparation of quinones by oxidizing polynuclear aromatic hydrocarbons with a ceric salt. As a result, it has been found that, as is evident from the results of experiments given hereinafter in Table 1, chlorobenzene and an alkylbenzene, such as tert-butylbenzene, in which a tertiary carbon atom of a tertiary alkyl group having from 4 to 7 carbon atoms is bonded to a phenyl group, are unreactive with ceric sulfate, quite stable under the reaction condition for oxidation with the ceric salt, and capable of dissolving the polynuclear aromatic hydrocarbon starting material such as naphthalene and the quinone product such as 1,4-naphthoquinone very well, and yet these organic solvents have specific gravities substantially smaller than the specific gravity of the relatively highly concentrated aqueous solution of cerous and ceric salts suitable for the oxidation reaction, and they are suitable as a solvent for liquid separation wherein the quinone formed by the reaction will be dissolved in the solvent constituting an upper layer. Thus, the present invention is based on the discovery that chlorobenzene and the tert-alkylbenzene are superior in the above respects as inert organic solvents immiscible with water, suitable for the preparation of quinones by the oxidation reaction of polynuclear aromatic hydrocarbons with a ceric salt, particularly from the viewpoint of industrial application.

Namely, the present invention provides a process for preparing a quinone, which comprises reacting a polynuclear aromatic hydrocarbon and a ceric salt in an aqueous acid solution in the presence of an organic solvent selected from the group consisting of chlorobenzene and an alkylbenzene represented by the general formula:

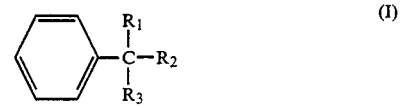

where each of $R_1$, $R_2$ and $R_3$ is an alkyl group and the total carbon number of the alkyl groups is from 3 to 6.

Hereinafter, the alkylbenzene of the above formula I to be used in the present invention, may be referred to as "a tert-alkylbenzene having a tertiary alkyl group of 4 to 7 carbon atoms".

Now, the present invention will be described in detail with reference to the preferred embodiments.

As the polynuclear aromatic hydrocarbon to be used as the starting material for the process for the preparation of the quinone according to the present invention, there may be mentioned, for instance, naphthalene, anthracene, ethylanthracene, phenanthrene, biphenyl or pyrene. According to the process of the present invention, quinones corresponding to the respective starting materials are obtainable as the products. For instance, 1,4-naphthoquinone is obtainable from naphthalene, 9,10-anthraquinone from anthracene, 9,10-phenanthrene quinone from phenanthrene, and 2-phenylbenzoquinone from biphenyl. The process of the present invention is particularly useful for the industrial production of 1,4-naphthoquinone.

As the ceric salt to be used as the oxidizing agent in the present invention, there may be mentioned, for instance, a mineral acid salt such as ceric sulfate, nitrate or perchlorate, ceric acetate, ceric chloroacetate, ceric fluoroacetate or ceric methane sulfonate.

In order to maintain the aqueous solution of the ceric salt for the oxidation reaction of the present invention under a stabilized condition, the aqueous acid solution has to be adequately acidic. As the acid, there may be used any acid corresponding to the cation constituting the above-mentioned ceric salt. A mineral acid, especially sulfuric acid, is particularly preferred from the viewpoint of the stability for the regeneration of the ceric salt by electrolytic oxidation of the cerous salt formed as a reduction product as a result of the oxidation reaction with the ceric salt. The concentration of the acid is selected usually within a range of from 5 to 15%, preferably from 6 to 12%.

The concentration of the ceric salt in the aqueous acid solution is not critical. For instance, it may be used in an amount beyond its solubility, i.e. in a slurry state, at the initial stage of the reaction. However, it is usual to conduct the reaction at a ceric salt concentration of at least 0.1 mol/l, preferably at least 0.3 mol/l and at most the maximum solubility. For instance, in a reaction system of ceric sulfate-aqueous sulfuric acid solution, the reaction is normally conducted at a ceric sulfate concentration of from 0.1 to 0.6 mol/l.

In the tert-alkylbenzene having a tertiary alkyl group of 4 to 7 carbon atoms to be used in the present invention as an inert organic solvent immiscible with water, and represented by the formula:

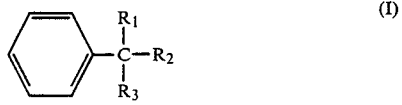

(I)

where $R_1$, $R_2$ and $R_3$ are as defined above, $R_1$, $R_2$ and $R_3$ include straight-chained and branched alkyl groups, but they are usually selected from straight-chained alkyl groups. As such a tert-alkylbenzene, there may be mentioned, for instance, tert-butylbenzene, tert-pentylbenzne, 1,1-dimethylbutylbenzene (i.e. tert-hexylbenzene) or 1,1 dimethylpentylbenzene (i.e. tert-heptylbenzene). Whereas, if the total carbon number of $R_1$, $R_2$ and $R_3$ in the formula I exceeds 6, i.e. if the carbon number of the tertiary alkyl group exceeds 7, the boiling point of the solvent tends to be so high that it becomes difficult to recover the solvent, and the solubility of the quinone products therein tends to decrease, such being undesirable.

As the organic solvent for the process of the present invention, chlorobenzene may also be used in addition to the above tert-alkylbenzenes. These solvents may be used alone or in combination as a mixture. The solvent is usually used in an amount sufficient to dissolve the polynuclear aromatic hydrocarbon starting material. Usually, the amount of the solvent is adjusted so that the concentration of the dissolved starting material be at least 1%. In order to increase the reaction speed, the amount of the solvent should preferably be adjusted so that the concentration of the starting material at the reaction temperature is close to its maximum solubility. For instance, when naphthalene is used as the starting material, the solvent is used in an amount sufficient to bring the concentration of the dissolved naphthalene to a level of from 20 to 60%, usually from 40 to 50%.

The process of the present invention is conducted usually at a reaction temperature of from 30° to 80° C., preferably from 40° to 60° C., for from 10 minutes to 2 hours although the reaction time varies depending upon the stirring conditions, the concentration of the starting material and the reaction temperature. If the reaction temeprature is lower than 30° C. , the reaction speed tends to be slow, and if the temperature exceeds 80° C., the production of by-products tends to increase. The reaction rate of the starting material can be increased to a level as high as almost 100% for a single reaction operation. However, in many cases, it is more advantageous from the industrial point of view to shorten the reaction time for one operation by controlling the reaction rate of the starting material to a level of 50% and using the unreacted starting material (e.g. naphthalene) and the above-mentioned inert organic solvent as a solvent mixture, so that the formed quinone dissolved in the solvent mixture is then separated by a method wherein the solvent mixture containing the quinone is subjected per se to a next reaction for the quinone whereby the quinone is converted to a secondary product soluble in water and separated into an aqueous layer, or by any other method, and after an addition of a necessary amount of the starting material (e.g. naphthalene), the solvent mixture is recycled for the reaction with the ceric salt, this operation being repeated until the reaction rate of the starting material reaches substantially a level of almost 100%.

The process for the preparation of the quinone according to the present invention is usually conducted in the following manner. Namely, an aqueous sulfuric acid solution containing a predetermined amount of a ceric salt such as ceric sulfate, is reacted with a solution of the starting material such as naphthalene in the above-mentioned inert organic solvent immiscible with water according to the present invention, for a predetermined period of time under stirring at a predetermined temperature. Then, the solvent layer is separated from the aqueous layer. Some of the product still remaining in the aqueous layer is extracted with the above-mentioned organic solvent and combined to the separated solvent layer. The combined solvent layer is then treated depending upon the particularly purpose. For instance, for the purpose of obtaining a quinone such as 1,4-naphthoquinone, the solvent is removed under reduced pressure to obtain the product by precipitation or drying. Whereas, for the purpose of using it for the subsequent reaction step, the solvent layer is subjected to a proper treatment such as washing with water before subjecting it to the reaction step. The above process may be conducted by a multi-stage countercurrent process instead of conducting the above-mentioned reaction steps and the separation steps for the separation of the solvent layer from the aqueous layer by a combination of plurality of reactors and separation tanks.

In the aqueous layer separated from the solvent layer in the above process, a cerous salt (i.e. a cerium III salt) formed by the reaction is present as the major component. In order to use this aqueous layer for the subsequent reaction, it is necessary to oxidize and regenerate the cerous salt to the ceric salt. As such a regeneration method, a chemical regeneration method by means of hydrogen peroxide has been proposed, but it is more common to employ a method by means of electrolytic oxidation. For instance, as disclosed in Japanese Examined Patent Publication No. 34978/1974, the cerous salt is converted to the ceric salt by electrolytic oxidation wherein the aqueous solution of the cerous salt formed by the reaction, is supplied to a batch-system or continuous-system electrolytic cell provided with electrodes made of an inert conductive material such as platinum, platinum-plated titanium or carbon. In this electrolysis, it is preferred to provide a porous partition wall or an ion exchange membrane between the electrodes. The electrolysis is usually conducted at a temperature of from 40° to 60° C. in view of the corrosion resistance of the material constituting the elecrolytic cell. This electrolytic temperature coincides with the temperature condition of the process of the present invention, and accordingly the regeneration method by means of the above electrolytic oxidation can be conducted industrially and economically.

In the regeneration process by means of the electrolytic oxidation, it is necessary from the industrial point of view to maintain the current efficiency at a high level. Accordingly, it is not usually economical to bring the cerous salt concentration to zero, and it is usual that the electrolysis is completed in such a state where the cerous salt still remains, and the aqueous acid solution of the ceric salt which contains a certain amount of the cerous salt, will be supplied to the above-mentioned reaction step.

According to another aspect of the present invention, the reaction of the polynuclear aromatic hydrocarbon and the ceric salt is conducted in the presence of tetralin.

Namely, when e.g. naphthalene and ceric sulfate are reacted in an aqueous sulfuric acid solution by means of the inert organic solvent, it is likely that after the reaction, there will be formed between the solvent layer and the aqueous layer, a muddy layer of a mixture comprising the solvent, water and the cerous sulfate crystals formed by the reaction. This muddy layer is likely to form in either a slurry method wherein the concentration of ceric sulfate is maintained to be high so that cerous sulfate crystals will precipitate after the reaction, or a solution method wherein no cerous sulfate will precipitate after the reaction. The formation of such a muddy layer makes it difficult to separate the solvent layer from the aqueous layer after the reaction and tends to lead to a loss of expensive cerium and 1,4-naphthoquinone. Any attempt for the recovery of cerium and 1,4-naphthoquinone from the muddy layer, involves cumbersome steps which add to the cost, and is not practical.

The present inventors have found that when tetralin is used as an inert organic solvent or tetralin is used in combination with the above-mentioned inert organic solvent, the formation of the above-mentioned muddy layer can be minimized, and the separation of the solvent layer from the aqueous layer after the reaction can thereby be facilitated. Thus, according to the second aspect of the present invention, the process of the present invention is conducted in the presence of tetralin.

In the case where tetralin is used in the form of a mixture with other organic solvent, the content of tetralin in the organic solvent mixture is usually at least about 10%, preferably at least 15% although the content may vary depending upon the type of the other organic solvent. Further, in view of the reaction of tetralin with the ceric salt, the tetralin content is selected within a range of at most 50%, preferably at most 30%.

When tetralin is used in combination with other organic solvent, the process of the present invention is conducted at a temperature of from 20° to 60° C., preferably from 30° to 55° C., for from 10 minutes to 2 hours although the reaction time may vary depending upon the stirring condition, the concentration of the starting material and the reaction temperature. If the reaction temperature is lower than 30° C., particularly 20° C., the reaction speed tends to be slow, and if the temperature exceeds 60° C., tetralin is likely to be oxidized.

Now, the present invention will be described in further detail with reference to Experiment and Examples. In this specification, "parts" and "%" mean "parts by weight" and "% by weight" unless otherwise specifically specified. Further, in the Examples, "(molar %)" following the amount of the product or the unreacted naphthalene means a molar % relative to the starting material (e.g. naphthalene).

Experiment

The reactivity of various solvents with ceric sulfate was tested. Namely, 40.7 g of ceric sulfate was dissolved in 289 g of a 8% sulfuric acid aqueous solution, and 10 g of each solvent identified in Table 1 was added to the solution. The mixture was stirred at 60° C., and the consumption rate of ceric sulfate was examined to obtain the reaction rate of ceric sulfate (i.e. the rate for the formation of cerous sulfate by the reaction of ceric sulfate with each solvent). The results, the specific gravities of the respective solvents and the applicability of each solvent to the process of the present invention and the reason therefor are presented in Table 1.

TABLE 1

| Organic solvents immiscible with water | Reaction rate of ceric sulfate (mol %/hr) | Specific gravity 20° C. | Applicability of the present invention and the reason therefor | |
|---|---|---|---|---|
| | | | Applicability | Reason |
| Benzenes | | | | |
| 1. tert-Butylbenzene | 0 | 0.87 | Yes | No reactivity, small specific gravity |
| 2. tert-Alkylbenzene (The tert-alkyl group has from 5 to 7 Carbon atoms.) | 0 | 0.86 | " | No reactivity, small specific gravity |
| 3. Chlorobenzene | 0 | 1.10 | " | No reactivity, small specific gravity |
| 4. Benzene | 1 | 0.88 | No | Reactive |
| 5. Ethylbenzene | 2 | 0.87 | " | " |
| 6. Cumene | 18 | 0.86 | " | " |
| 7. Xylene | 15 | 0.88 | " | " |
| Aliphatic hydrocarbons | | | | |
| 1. Dichloroethane (Ethylene dichloride) | — | 1.25 | " | Great specific gravity, susceptible to decom- |

TABLE 1-continued

| Organic solvents immiscible with water | Reaction rate of ceric sulfate (mol %/hr) | Specific gravity 20° C. | Applicability of the present invention and the reason therefor | |
|---|---|---|---|---|
| | | | Applicability | Reason |
| 2. 1,1,2-trichloro-ethane | — | 1.44 | " | position Great specific gravity, susceptible to decomposition |
| Other | | | | |
| Carbon tetrachloride | — | 1.595 | " | Great specific gravity |

EXAMPLE 1

Into a bottom-discharge type cylindrical glass reactor having a capacity of 500 ml and equipped with a stirrer with flat turbine vanes and a temperature controlling means, 39.5 g of ceric sulfate and 338 g of 8% sulfuric acid were introduced, and the temperature was raised to 55° C. Then, 5.08 g of naphthalene and 12 g of tert-butylbenzne were added thereto, and the mixture was stirred at a low speed to dissolve napthalene. Then, the rotational speed of the stirrer was raised to 650 rpm, and the reaction was conducted at a temperature of 60° C. for 30 minutes.

After the reaction of 30 minutes, the rotational speed of the stirrer was reduced to 15 rpm to separate the oil layer and the aqueous layer, and after being left to stand still, the aqueous layer was withdrawn from the nozzle at the bottom. The aqueous layer thus withdrawn was extracted twice by 20 ml of tert-butylbenzene, and the extraction oil layer thereby obtained was combined with the previously separated oil layer. The formed 1,4-naphthoquinone and naphthalene in the total tert-butylbenzene solution were quantitatively analyzed by a high speed liquid chromatography. On the other hand, with respect to the by-product phthalic acid dissolved in the above aqueous layer, 2.00 g of a sample solution was taken from the above-mentioned aqueous layer, and after an addition of an internal standard solution, a solvent mixture of methanol-water corresponding to the composition of the developer used in the high speed liquid chromatography, was added thereto, whereby cerous sulfate and ceric sulfate were precipitated, then the crystals were separated by filtration and the filtrate was subjected to high speed liquid chromatography to quantitatively analyze the by-product phthalic acid. As the results, it was found that the amount of formed 1,4-naphthoquinone was 2.96 g (47.1 molar %), the amount of formed phthalic acid was 0.09 g (1.4 moalr %) and the amount of unreacted naphthalene was 2.58 g (50.8 molar %). Namely, the yield of 1,4-naphthoquinone relative to reacted naphthalene was 95.8 molar %, and the yield of the by-product phthalic acid was 2.8 moalr % relative to reacted naphthalene.

Then, the aqueous layer from which 1,4-naphthoquinone was extracted as mentioned above, was continuously supplied to an anolyte recycling line defined by an ion exchange membrane, and while using sulfuric acid as the catholyte, electrolytically oxidized with use of a platinum electrode until the concentration of ceric sulfate became 0.5 mol/l. The sulfuric acid solution of ceric sulfate obtained by the electrolytic treatment, was supplied to the subsequent naphthalene oxidation reaction of the process of the present invention, whereby similar results were obtained.

EXAMPLE 2

Into a 200 ml Erlenmeyer flask with ground stopper, 4.10 g of ceric sulfate and 28.0 g of 8% sulfuric acid were introduced, and the mixture was stirred with a Teflon-coated stirrer. After raising the temperature to 55° C., 0.525 g of naphthalene and 0.6 g of Hyzol P (i.e. a solvent mixture comprising tert-alkylbenzenes having tert-alkyl groups of 5 to 7 carbon atoms; manufactured by Nippon Petrochemicals Co., Ltd.) were added, after the flask was closed with a stopper, the reaction was conducted at 60° C. for 30 minutes under vigorous stirring at 1000 rpm.

After the reaction for 30 minutes, 30 ml of Hyzol P was further added, and the mixture was stirred at room temperature for about 2 minutes and then left to stand still. The aqueous layer was transferred to a separating funnel by means of a pipette, whereby the aqueous layer and the oil layer were separated.

Naphthalene and 1,4-naphthoquinone in the aqueous layer separated into the separating funnel, were extracted twice with 30 ml of Hyzol P, and the extracted Hyzol P solution was combined with the Hyzol P solution of the previously separated oil layer to obtain a total Hyzol P solution.

Then, the total Hyzol P solution was treated in the same manner as in Example 1 and then quantitatively analyzed to obtain the results such that the amount of formed 1,4-naphthoquinone was 0.270 g (41.7 molar %), the amount of by-product phthalic acid was 0.0081 g (1.2 molar %) and the amount of unreacted naphthalene was 0.298 g (56.8 molar %). Namely, the yield of 1,4-naphthoquinone was 96.5 molar % relative to reacted naphthalene, and likewise the yield of phthalic acid was 2.8 molar % relative to reacted naphthalene.

EXAMPLE 3

Into a bottom-discharge type cylindrical glass reactor having a capacity of 500 ml and equipped with a stirrer with flat turbine vanes and a temperature controlling means, 39.4 g of ceric sulfate, 25.6 g of cerous sulfate and 310 g of 8% sulfuric acid were introduced, and the temperature was raised to 55° C. Then, 5.06 g of naphthalene and 12 g of tert-butylbenzene were added, and the mixture was stirred at a low speed to dissolve naphthalene. Then, the rotational speed of the stirrer was raised to 650 rpm, and the reaction was conducted for 30 minutes at a reaction temperature of 60° C.

After the reaction for 30 minutes, the rotational speed of the stirrer was reduced to 15 rpm to separate the oil layer and the aqueous layer, and the mixture was left to stand still. Then, the aqueous layer was withdrawn from the nozzle at the bottom.

Then, the after treatment was conducted in the same manner as in Example 1, and then the quantitative analysis was conducted, whereby it was found that the amount of formed 1,4-naphthoquinone was 2.94 g (47.1 molar %), the amount of by-product phthalic acid was 0.10 g (1.5 molar %) and the amount of unreacted naphthalene was 2.59 g (51.2 molar %). Namely, the yield of 1,4-naphthoquinone was 96.5 molar % relative to reacted naphthalene, and the yield of by-product phthalic acid was 3.1 molar % relative to reacted naphthalene.

COMPARATIVE EXAMPLE 1

The reaction was conducted in the same manner as in Example 3 except that ethylene dichloride was used instead of tert-butylbenzene. After the reaction for 30 minutes, the rotational speed of the stirrer was reduced to 15 rpm to conduct stirring at low speed, and then the mixture was left to stand still, whereby an aqueous layer was formed as an upper layer and a slurry layer combined with the descended oil layer of ethylene dichloride having a great specific gravity, was formed as the lower layer. It was difficult to separate the oil layer from the precipitates (cerous sulfate).

EXAMPLE 4

Into a glass-lined reactor equipped with a stirrer with flat turbine vanes, a buffle and a temperature controlling means, 8.20 parts of ceric sulfate, 5.10 parts of cerous sulfate and 60 parts of 6.5% sulfuric acid, were introduced, and the temperature was raised to 50° C. Then, 1.05 parts of naphthalene and 2.0 parts of chlorobenzene were added, and the mixture was stirred at a low speed to dissolve naphthalene.

Then, the reaction and the after treatment were conducted in the same manner as in Example 3, and the quantitative analysis was conducted, whereby it was found that the amount of formed 1,4-naphthoquinone was 0.551 parts (42.5 molar %), the amount of by-product phthalic acid was 0.012 part (0.9 molar %) and the amount of unreacted naphthalene was 0.591 part (56.3 molar %). Namely, the yield of 1,4-naphthoquinone was 97.3 molar % relative to reacted naphthalene, and the yield of by-product phthalic acid was 2.0 molar % relative to reacted naphthalene.

EXAMPLE 5

Into a 100 ml Erlenmeyer flask, 2.8 g of an inert organic solvent comprising tert-butylbenzene (hereinafter referred to as "TBB") or chlorobenzene (hereinafter referred to as "Cl-Bz") and/or tetralin (hereinafter referred to as "TLN") in the proportion as identified in Table 2, was fed, and naphthalene (hereinafter referred to as "Np") [F.P.: 79.8° C.; sulfur content: 0.23% (i.e. 0.98% as thionaphthene)] was added in the predetermined amount as identified in Table 2. Then, 51.8 ml of an aqueous solution comprising 2.95 g (0.1002 mol/l) of cerous sulfate ($Ce_2(SO_4)_3$), 7.23 g (0.420 mol/l) of ceric sulfate ($Ce(SO_4)_2$, 4.51 g of sulfuric acid and 48.52 g of water (the sulfuric acid concentration as the aqueous sulfuric acid solution being 8.5%), was added, the mixture was reacted for 30 minutes at 50° C. under stirring with a magnetic stirrer at 1000 rpm. After the reaction, the mixture was left to stand still, whereby the formation of a muddy layer at the interface between the organic solvent layer (i.e the oil layer) and the aqueous layer, was observed. Then, 20 ml of benzene was added as unextraction solvent, and the reaction products were extracted. The aqueous layer separated from the oil layer was extracted twice with 20 ml of benzene, and the extracted solution was combined with the previously separated oil layer. The combined total oil layer was analyzed by gas chromatography, and the aqueous layer was analyzed by high speed liquid chromatography. The results thereby obtained are shown in Table 2.

TABLE 2

| | Inert organic solvents | | | | | Yield (molar % relative to reacted Np) | |
|---|---|---|---|---|---|---|---|
| | Solvent other than TLN | | TLN | Naphthalene | Interfacial muddy layer | Conversion of Np | | Phthalic |
| No. | Name | (%) | (%) | (g) | formation* | (molar %) | 1,4-naphthoquinone | acid |
| 1 | — | 0 | 100 | 2.135 | None | 16.8 | 95.7 | 1.9 |
| 2 | TBB | 100 | 0 | 2.147 | (++) | 17.7 | 97.0 | 3.0 |
| 3 | " | 93.5 | 7.5 | 2.160 | (+) | 18.0 | 97.4 | 2.6 |
| 4 | " | 90 | 10 | 2.127 | (−) | 19.0 | 97.4 | 2.6 |
| 5 | Cl—Bz | 100 | 0 | 2.142 | (++) | 17.1 | 95.8 | 2.3 |
| 6 | " | 93.5 | 7.5 | 2.155 | (++) | 17.3 | 96.9 | 2.7 |
| 7 | " | 90 | 10 | 2.146 | (+) | 17.2 | 97.5 | 2.3 |
| 8 | " | 80 | 20 | 2.163 | (−) | 16.3 | 96.9 | 2.8 |

*(−): trace, (+): small amount, (++): substantial amount

EXAMPLE 6

Into a 100 liter glass-lined reactor equipped with a stirrer, 80 liter of an aqueous phase comprising $Ce(SO_4)_2$ (at the concentration identified in Table 3), $Ce_2(SO_4)_3$ (0.15 mol/l) and $H_2SO_4$ (8.5% aqueous solution), was fed, and 3.31 kg of naphthalene (F.P.: 79.8° C.; thionaphthene content: 0.98%) and 4.28 kg of a solvent comprising TBB and/or TLN in the proportion identified in Table 3, were added. The mixture was stirred and reacted at 50° C. for 30 minutes. The results thereby obtained are shown in Table 3.

TABLE 3

| No. | Inert organic solvents TBB (Kg) | Inert organic solvents TLN (Kg) | Concentration of Ce(SO4)2 in the aqueous phase (mol/l) | Conversion of Np (%) | Yield of 1,4-naphthoquinone (molar % relative to reacted Np) | Yield of phthalic acid (molar % relative to reacted Np) | Formation of interfacial muddy layer (Kg)/oil phase (Kg) | Formation of interfacial muddy layer (% relative to the weight of the oil phase) |
|---|---|---|---|---|---|---|---|---|
| 9 | 4.28 | 0 | 0.310 | 14.0 | 97.9 | 1.9 | 0.27/7.4 | 3.6 |
| 10 | 3.42 | 0.86 | 0.316 | 16.8 | 98.0 | 1.8 | 0.018/7.4 | 0.2 |
| 11 | 0 | 4.28 | 0.270 | 11.2 | 98.0 | 1.8 | trace | trace |

It is evident from the results of Tables 2 and 3 that the formation of a muddy layer at the interface between the oil layer and the aqueous layer can be substantially reduced by the presence of TLN. More specifically, the formation of the interfacial muddy layer can be reduced to a level of a small amount or a trace amount when TLN is added in an amount of at least 10% in the case of TBB or at least 20% in the case of Cl-Bz. Thus, the separation of the oil layer from the aqueous layer can be substantially facilitated by the presence of TLN, and the recovery of cerium and formed 1,4-naphthoquinone can be readily conducted without no substantial loss.

Further, in the case where at least a part of TBB solvent was substituted by TLN, the solubility of formed 1,4-naphthoquinone at 50° C. was measured. The results are shown in Table 3. As is evident from Table 4, the solubility was improved by about 10 to 30%. This brings about an industrial advantage such that it is possible to reduce the amount of the organic solvent by the use of TLN.

TABLE 4

| Oil phase components TBB (parts by weight) | Oil phase components TLN (parts by weight) | Oil phase components Np (parts by weight) | Solubility of 1,4-naphthoquinone (50° C.) (% relative to the oil phase) |
|---|---|---|---|
| 100 | 0 | 60 | 13.0 |
| 80 | 20 | 60 | 14.1 |
| 50 | 50 | 60 | 14.7 |
| 0 | 100 | 60 | 16.5 |

We claim:

1. A process for preparing a quinone, which comprises reacting a polynuclear aromatic hydrocarbon and a ceric salt in an aqueous acid solution in the presence of an organic solvent selected from the group consisting of chlorobenzene and an alkylbenzene represented by the general formula:

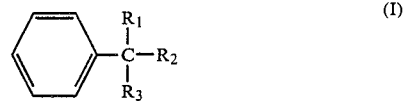

(I)

where each of $R_1$, $R_2$ and $R_3$ is an alkyl group and the total carbon number of the alkyl groups is from 3 to 6.

2. The process according to claim 1, wherein the polynuclear aromatic hydrocarbon is naphthalene and the quinone is 1,4-naphthoquinone.

3. The process according to claim 1, wherein the ceric salt is ceric sulfate.

4. The process according to claim 1, wherein the aqueous acid solution is an aqueous sulfuric acid solution.

5. The process according to claim 1, wherein the reaction is conducted in the presence of tetralin.

6. The process according to claim 5, wherein tetralin is present in an amount of from about 10 to 50% by weight in the total organic solvent.

7. The process according to claim 5, wherein tetralin is present in an amount of from about 15 to 30% by weight in the total organic solvent.

8. The process according to claim 5, wherein the reaction is conducted at a temperature of from 20° to 60° C.

9. The process according to claim 5, wherein the reaction is conducted at a temperature of from 30° to 55° C.

* * * * *